(12) United States Patent
Ohara et al.

(10) Patent No.: US 6,569,989 B2
(45) Date of Patent: May 27, 2003

(54) PROCESS FOR PRODUCING LACTIDE AND PROCESS FOR PRODUCING POLYLACTIC ACID FROM FERMENTED LACTIC ACID EMPLOYED AS STARTING MATERIAL

(75) Inventors: Hitomi Ohara, Kyoto (JP); Masahiro Ito, Kusatsu (JP); Seiji Sawa, Otsu (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 10/020,907

(22) Filed: Dec. 19, 2001

(65) Prior Publication Data

US 2002/0132967 A1 Sep. 19, 2002

(30) Foreign Application Priority Data

Jan. 31, 2001 (JP) ........................................ 2001-024651

(51) Int. Cl.$^7$ .............................................. C08G 63/08
(52) U.S. Cl. ...................................................... 528/354
(58) Field of Search ................................ 528/354, 355, 528/359

(56) References Cited

U.S. PATENT DOCUMENTS

| | | | | |
|---|---|---|---|---|
| 4,666,849 A | * | 5/1987 | Daeschel et al. | 435/253 |
| 5,453,365 A | | 9/1995 | Sterzel et al. | 435/135 |
| 6,313,319 B1 | * | 11/2001 | Ohara et al. | 549/274 |
| 6,326,458 B1 | * | 12/2001 | Gruber et al. | 528/354 |

FOREIGN PATENT DOCUMENTS

| | | |
|---|---|---|
| EP | 0658628 | 11/1994 |
| JP | 07138253 | 5/1995 |
| JP | 07173264 | 7/1995 |
| JP | 08027255 | 1/1996 |
| JP | 11209370 | 8/1999 |
| WO | WO 91/11527 | 8/1991 |
| WO | WO 98/23579 | 6/1998 |

OTHER PUBLICATIONS

Biosci. Biotech. Bicochem., 60(4), pp. 692–693, Hitomi Ohara et al "NAD–Specific 6–Phosphogluconate Dehydrogenase in Lactic Acid Bacteria", Oct. 1995.*
Bercey's Manual of Systematic Bacteriology, vol. 2, pp. 1070–1071, Section 12, (1986), "Genus Leuconostoc", ed. Ellen L. Garvie.*
Bercey's Manual of Systematic Bacteriology, vol. 2, pp. 1208–1213, Section 14, (1986), "Regular, Nonsporing Gram–Positive Rods", Otto Kander et al.*

* cited by examiner

Primary Examiner—P. Hampton-Hightower
(74) Attorney, Agent, or Firm—Rader Fishman & Grauer, PLLC (57) ABSTRACT

According to the present invention, a process for consistently producing lactide from ammonium lactate obtained by lactic fermentation, and a process for consistently producing polylactic acid from ammonium lactate obtained by lactic fermentation, are provided. A process for producing lactide, which comprises the steps of: (1) synthesizing lactate ester from ammonium lactate obtained by lactic fermentation; (2) polycondensing the lactate ester in the presence of a catalyst other than monobutyltin, whereby polylactic acid with a weight-average molecular weight of less than 15,000 (lactic acid prepolymer) is synthesized; and (3) depolymerizing the polylactic, whereby lactide is produced. A process for producing polylactic acid, which comprises the additional step of (4) ring-opening polymerizing said lactide, whereby polylactic acid is obtained. A process for producing lactate ester from ammonium lactate obtained by lactic fermentation.

16 Claims, 3 Drawing Sheets

PROCESS FOR PRODUCING LACTIDE AND PROCESS FOR PRODUCING POLYLACTIC ACID FROM FERMENTED LACTIC ACID EMPLOYED AS STARTING MATERIAL

BACKGROUND OF THE INVENTION

1. Field of the Invention

The present invention relates to a process for producing lactide and a process for producing polylactic acid from fermented lactic acid employed as a starting material, and to a process for producing lactide and a process for producing polylactic acid from ammonium lactate obtained by lactic fermentation. Also, the present invention relates to a process for producing lactate ester from ammonium lactate obtained by lactic fermentation.

Lactic acid includes L-lactic acid, D-lactic acid, and a mixture of L-lactic acid and D-lactic acid. Lactide is a cyclic dimer of the lactic acid, and lactide is particularly useful as a starting material for producing polylactic acid. The polylactic acid is a polymer in which the lactic acid is contained as a major constitutional monomer, and the polylactic acid includes not only a homopolymer of the lactic acid but also a copolymer of the lactic acid with other monomers. The polylactic acid is useful as a biodegradable plastic derived from biomass employed as a starting material.

2. Description of the Related Art

Traditionally, the production of polylactic acid has been performed by a dehydration condensation directly from lactic acid, a dealcohol condensation from lactate ester, or a ring-opening polymerization of lactide.

With regard to the production of polylactic acid from lactate ester, for example, the specification of U.S. Pat. No. 2,534,255 discloses a method producing hydroxy polyester from hydroxycarboxylate ester in the presence of a catalyst for esterification.

Japanese Laid-open Patent Publication No. H07-173264 (1995) discloses a method condensing lactate ester to produce polylactic acid with a weight-average molecular weight of 15,000 or above. There is no description in which lactide is synthesized from said polymerized product. It is necessary to consume great time for producing the polylactic acid with a weight-average molecular weight of 15,000 or above.

Japanese Patent Publication (B2) No. 3024907 discloses a process polycondensing lactate ester in a batch type reactor while removing generated alcohol, and further polycondensing the obtained oligomer in a screw type extruding machine while removing generated alcohol so as to produce polylactic acid from the lactate ester. There is no description in which lactide is synthesized from said polymerized product.

Japanese Laid-open Patent Publication No. H10-36366 (1998) discloses a process synthesizing lactate ester from synthesized lactic acid (DL-lactic acid), dealcoholizing the lactate ester to synthesize a lactic acid oligomer, and subsequently synthesizing lactide.

Japanese Laid-open Patent Publication No. H11-209370 (1999) discloses a process for producing lactide, which comprises dealcoholizing lactate ester in the presence of a monobutyltin compound to produce a composition containing polylactic acid or a composition containing polylactic acid and lactide, and then heating the composition in the presence of a monobutyltin compound.

Besides, it has been previously known that ammonium lactate is directly esterified with alcohol (in INDUSTRIAL AND ENGINEERING CHEMISTRY, VOL.44, NO.9, 2189–2191, September 1957).

Japanese Laid-open Patent Publication No. H06-311886 (1994) discloses a process adding butanol or pentanol to ammonium lactate generated by fermentation, and adding mineral acid thereto at the later stage of the reaction to proceed reaction further, thereby recovering lactate ester with recovering ammonia.

Furthermore, Japanese Patent Publication (B2) No. 2830896 discloses a process synthesizing an oligomer from lactic acid used as a starting material, refluxing the oligomer to synthesize an oligomer with higher degree of polymerization, and producing lactide from the oligomer with higher degree of polymerization. There is no disclosure of a process in which polycondensation is conducted employing lactate ester while refluxing a monomer of the lactate ester and an oligomer thereof.

SUMMARY OF THE INVENTION

Thus, a process which comprises synthesizing a lactic acid oligomer in which lactate ester derived from fermented lactic acid is employed as a starting material, and depolymerizing the lactic acid oligomer to produce lactide, and a process which comprises synthesizing a lactic acid oligomer in which lactate ester derived from fermented lactic acid is employed as a starting material, depolymerizing the lactic acid oligomer to produce lactide, and producing polylactic acid from the lactide, have never been known.

Further, in a synthesis of lactate ester from lactic fermentation, producing lactic acid and ethanol by means of hetero-type lactic fermentation while neutralizing with ammonia, and esterifying this lactic acid, have never been known. Hetero-lactic acid bacteria produce lactic acid and ethanol from glucose, and produce lactic acid and acetic acid from xylose.

Hitherto, in producing lactic acid, lactic acid was obtained by steps of performing lactic fermentation of hexose (glucose) or sucrose (consisting of glucose and fructose); neutralizing with calcium carbonate; concentrating to allow calcium lactate to precipitate; liberating with sulfuric acid to produce crude lactic acid; further converting into ester with methanol or ethanol; and distilling the ester followed by hydrolyzing the ester to produce lactic acid. According to this process, there were problems in which significant amounts of calcium sulfate were generated as a byproduct.

Accordingly, a process which comprises neutralizing with ammonia water or ammonia during lactic fermentation to obtain ammonium lactate, converting ammonium lactate into ester with alcohol followed by distilling, recovering ammonia, and hydrolyzing lactate ester, is developed.

Hitherto, there was no consistent process for producing polylactic acid from biomass. By completing the consistent process, cost for producing polylactic acid can be reduced. Namely, there were lots of useless steps conducted, because the production of polylactic acid was formerly considered to be separated from the production of lactic acid. Concretely, the useless step means a step of hydrolyzing lactate ester to produce lactic acid. Besides, by synthesizing polylactic acid from lactate ester, corrosive resistance required for a reactor can be mitigated, and significant contribution in a capital investment can be achieved. Because lactic acid has corrosive properties, especially in the case of concentrating or synthesizing lactide at a temperature exceeding 140° C., it has been necessary to use a reactor and a tube made of titanium or tantalum, or a reactor and a tube with glass lining. However, in the case of using lactate ester, it is not necessary to use a material with corrosive resistance for a reactor, thereby achieving drastic cost reduction in equipments of facilities.

In particular, there is a worldwide subject of how to utilize wood type biomass at present. In Japan, there is a subject of how to treat wastes such as old papers, construction waste materials, lumbers from thinning, rice straws and the others. In overseas, there is a stream to use wood materials as a starting material for fermentation because wood materials cannot be directly used as foodstuffs for people.

The wood type biomass includes cellulose and hemicellulose. As a method for saccharification of cellulose and hemicellulose, a sulfuric acid method, a high-pressure hot water method, and an enzyme method are in a stage of practical use. Sugar obtained by saccharification is hexose and pentose. The hexose is mainly glucose, and the pentose is mainly xylose.

By homo-type lactic fermentation, 1 mol of glucose is converted to 2 mols of lactic acid, which does not waste carbon atoms. Further, among the lactic acid bacteria, there are strains capable of producing 5 mols of lactic acid from 3 mol of xylose. Furthermore, by hetero-type lactic fermentation, 1 mol of glucose is converted to 1 mol of lactic acid and 1 mol of ethanol (in this case, 1 mol of carbon dioxide gas is generated). Namely, glucose is a particularly suitable starting material for synthesizing lactate ester.

On the other hand, by hetero-type lactic fermentation, 1 mol of lactic acid and 1 mol of acetic acid are produced from 1 mol of xylose. Thus, in the present invention, hetero-lactic fermentation is conducted while neutralizing with ammonia to generate lactic acid and acetic acid, and generated lactic acid and acetic acid are esterified with alcohol (ethanol) to synthesize esters that are isolated from a fermentation liquid as lactate ester and acetate ester, respectively.

In the case of allowing ammonium lactate to react with ethanol to produce ethyl lactate, there were problems in which yield is low and reaction slowly proceeds due to low boiling point of ethanol that is 78° C.

In the case of allowing ammonium lactate to react with hydrophobic alcohol such as butanol to produce lactate ester, there were problems in which yield is low in approximately 50% even if water is removed by means of a separator.

An object of the present invention is to provide a process for consistently producing lactide from ammonium lactate obtained by lactic fermentation, and a process for consistently producing polylactic acid from ammonium lactate obtained by lactic fermentation. Further, an object of the present invention is to provide a process for producing lactate ester from ammonium lactate obtained by lactic fermentation.

The present invention is a process for producing lactide, which comprises the steps of: (1) synthesizing lactate ester from ammonium lactate obtained by lactic fermentation; (2) polycondensing the lactate ester in the presence of a catalyst other than monobutyltin, whereby polylactic acid with a weight-average molecular weight of less than 15,000 (lactic acid prepolymer) is synthesized; and (3) depolymerizing the polylactic acid, whereby lactide is produced.

The present invention is said process for producing lactide, wherein the step (1) comprises: allowing the ammonium lactate obtained by lactic fermentation to react with alcohol, whereby lactate ester is synthesized; and recovering ammonia.

The present invention is said process for producing lactide, wherein the step (1) comprises: allowing the ammonium lactate obtained by lactic fermentation to react with alcohol other than alcohol of which the number of carbon atoms is 4 or 5, whereby lactate ester is synthesized; and recovering ammonia.

The present invention is said process for producing lactide, wherein the step (1) comprises: allowing the ammonium lactate obtained by lactic fermentation to react with ethanol under a pressurized condition, whereby ethyl lactate is synthesized; and recovering ammonia.

The present invention is said process for producing lactide, wherein the step (1) comprises: allowing an aqueous solution of the ammonium lactate obtained by lactic fermentation to react with alcohol of which the number of carbon atoms is 4 or more in a reactor under reflux, in which the alcohol is separable from water to form two layers with water;

trapping at least a portion of condensed water and at least a portion of condensed alcohol in a separator; discharging at least a portion of the water trapped in the separator as a lower layer; adding fresh water to the separator and returning at least a portion of the alcohol trapped in the separator as an upper layer into the reactor; and repeating this series of the procedures, whereby lactate ester is synthesized; and recovering ammonia.

The present invention is said process for producing lactide, wherein the step (1) comprises: allowing an aqueous solution of the ammonium lactate obtained by lactic fermentation to react with alcohol of which the number of carbon atoms is 4 or more in a reactor under reflux, in which the alcohol is separable from water to form two layers with water; distilling off a portion of the alcohol or the whole alcohol continuously; and adding fresh alcohol to the reactor, whereby lactate ester is synthesized; and recovering ammonia.

The present invention is said process for producing lactide, wherein the step (1) comprises: allowing the ammonium lactate obtained by lactic fermentation to react with ethanol; after completing the reaction, distilling off ethanol and ethyl lactate, respectively;

adding fresh ethanol to a remained solution of the ammonium lactate or adding fresh ethanol and fresh ammonium lactate obtained by lactic fermentation to the remained solution of the ammonium lactate; allowing the ammonium lactate to react with ethanol again; and repeating this reaction procedure, whereby ethyl lactate is synthesized; and recovering ammonia.

The present invention is said process for producing lactide, wherein the polycondensation in the step (2) is conducted while refluxing the lactate ester and/or the polylactic acid (lactic acid prepolymer) which is a polycondensed product of the lactate ester.

The present invention is said process for producing lactide, wherein the step (2) comprises: polycondensing the lactate ester, whereby the lactic acid prepolymer is obtained; and recovering generated alcohol.

The present invention is said process for producing lactide, wherein the step (2) comprises raising a temperature of a reactor continuously in the step of polycondensing the lactate ester.

The present invention is said process for producing lactide, wherein the step (1) comprises: culturing a microorganism capable of conducting hetero-lactic fermentation in a culture medium containing hexose while controlling a pH value with ammonia to produce the ammonium lactate and ethanol; and allowing the ammonium lactate to react with alcohol, whereby lactate ester is synthesized; and recovering ammonia.

The present invention is said process for producing lactide, wherein the step (1) comprises: culturing a microorganism capable of conducting hetero-lactic fermentation in a culture medium containing hexose while controlling a pH value with ammonia to produce the ammonium lactate and ethanol; and     allowing the ammonium lactate to react with alcohol other than alcohol of which the number of carbon atoms is 4 or 5, whereby lactate ester is synthesized; and recovering ammonia.

The present invention is said process for producing lactide, wherein the step (1) comprises: culturing a microorganism capable of conducting hetero-lactic fermentation in a culture medium containing pentose while controlling a pH value with ammonia to produce ammonium lactate and ammonium acetate;

allowing the ammonium lactate and the ammonium acetate to react with ethanol, whereby ethyl lactate and ethyl acetate are synthesized, respectively; recovering ammonia; and further removing ethyl acetate by distillation; and     wherein the step (2) comprises: polycondensing the ethyl lactate, whereby the lactic acid prepolymer is obtained; and recovering ethanol.

The present invention is said process for producing lactide, wherein the step (1) comprises: culturing a microorganism capable of conducting hetero-lactic fermentation in a culture medium containing pentose and hexose while controlling a pH value with ammonia to produce ammonium lactate, ethanol and ammonium acetate;

allowing the ammonium lactate and the ammonium acetate to react with ethanol, whereby ethyl lactate and ethyl acetate are synthesized, respectively; recovering ammonia; and further removing the ethyl acetate by distillation; and     wherein the step (2) comprises: polycondensing the ethyl lactate, whereby the lactic acid prepolymer is obtained; and recovering ethanol.

Also, the present invention is a process for producing polylactic acid, which comprises ring-opening polycondensing lactide obtained by any one of said process, whereby polylactic acid is obtained.

Further, the present invention is a process for producing ethyl lactate, which comprises allowing ammonium lactate obtained by lactic fermentation to react with ethanol under a pressurized condition, whereby ethyl lactate is synthesized.

The present invention is a process for producing lactate ester, which comprises: allowing an aqueous solution of ammonium lactate obtained by lactic fermentation to react with alcohol of which the number of carbon atoms is 4 or more in a reactor under reflux, in which the alcohol is separable from water to form two layers with water;

trapping at least a portion of condensed water and at least a portion of condensed alcohol in a separator; discharging at least a portion of the water trapped in the separator as a lower layer; adding fresh water to the separator and returning at least a portion of the alcohol trapped in the separator as an upper layer into the reactor; and repeating this series of the procedures, whereby lactate ester is synthesized.

The present invention is a process for producing lactate ester, which comprises: allowing an aqueous solution of ammonium lactate obtained by lactic fermentation to react with alcohol of which the number of carbon atoms is 4 or more in a reactor under reflux, in which the alcohol is separable from water to form two layers with water; distilling off a portion of the alcohol or the whole alcohol continuously; and adding fresh alcohol to the reactor, whereby lactate ester is synthesized.

The present invention is a process for producing lactic acid prepolymer, which comprises the steps of: (1) synthesizing lactate ester from ammonium lactate obtained by lactic fermentation; and (2) polycondensing the lactate ester in the presence of a catalyst other than monobutyltin, in which said polycondensation is conducted while refluxing the lactate ester and/or polylactic acid (lactic acid prepolymer) which is a polycondensed product of the lactate ester, whereby polylactic acid with a weight-average molecular weight of less than 15,000 (lactic acid prepolymer) is synthesized.

In the case of allowing ammonium lactate to react with ethanol to produce lactate ester, a method by adding, for example, 5 mols to 20 mols of ethanol based on 1 mol of ammonium lactate to shift equilibrium to the side of the ester can be considered.

Further, recovery yield of ethyl lactate can be increased by distilling off ethanol and generated ethyl lactate followed by adding a fresh lactic fermentation liquid and ethanol into the unreacted ammonium lactate remained in a reactor so as to perform reaction.

In this reaction, a reaction rate can be increased by pressurizing to raise a vapor pressure of ethanol and to raise a reaction temperature, because a boiling point of ethanol, 78° C., is low. Also, in this case, eliminated ammonia is removed to the outside of the system via a valve for controlling pressure. As a method of pressurizing, a method by utilizing a vapor pressure of ethanol it self and a method for pressurizing by an inert gas such as nitrogen gas are preferable.

In a method allowing ammonium lactate to react with butanol under reflux, if ammonia is saturated in water separated in a separator by vaporizing from a reactor followed by condensing, ammonia would be accumulated in butanol trapped in the separator as an upper layer, thereby becoming the reaction slow. Namely, it is considered that water trapped in the separator as a lower layer performs work for extracting ammonia existing in the upper layer butanol into the water side so as to reduce an amount of ammonia existing in butanol to be returned into the reactor. Consequently, by replacing the lower layer water trapped in the separator with fresh water, ammonia in the upper layer butanol is extracted with this fresh water. And, by returning butanol in which the ammonia content is reduced into the reactor, the reaction proceeds further.

According to the present invention, a process for consistently producing lactide from ammonium lactate obtained by lactic fermentation, and a process for consistently producing polylactic acid from ammonium lactate obtained by lactic fermentation, are provided. Further, according to the present invention, a process for producing lactate ester from ammonium lactate obtained by lactic fermentation is provided.

In the present process, ammonium lactate from lactic fermentation is esterified as it is, thereby eliminating the need of a procedure in which lactate salt is converted to a free form of lactic acid as former processes required. Consequently, steps in producing lactide and producing polylactic acid can be reduced, and lactide and polylactic acid can be produced in less expensive manner.

Furthermore, in the present process, neutral ammonium lactate is employed as a starting material, thereby eliminating the need to use a reactor and tube with acid resistance properties such as those made of titanium or glass. Therefore, the present process is economic because capital investment for production can be reduced, comparing with former methods that required a reactor and tube with acid resistance properties because a free form of lactic acid is used as a starting material.

DETAILED DESCRIPTION OF THE INVENTION

Next, the present invention will be explained by referring to the drawings.

(1) Step of Esterifying Fermented Lactic Acid and Removing Ammonia

Figure 1:
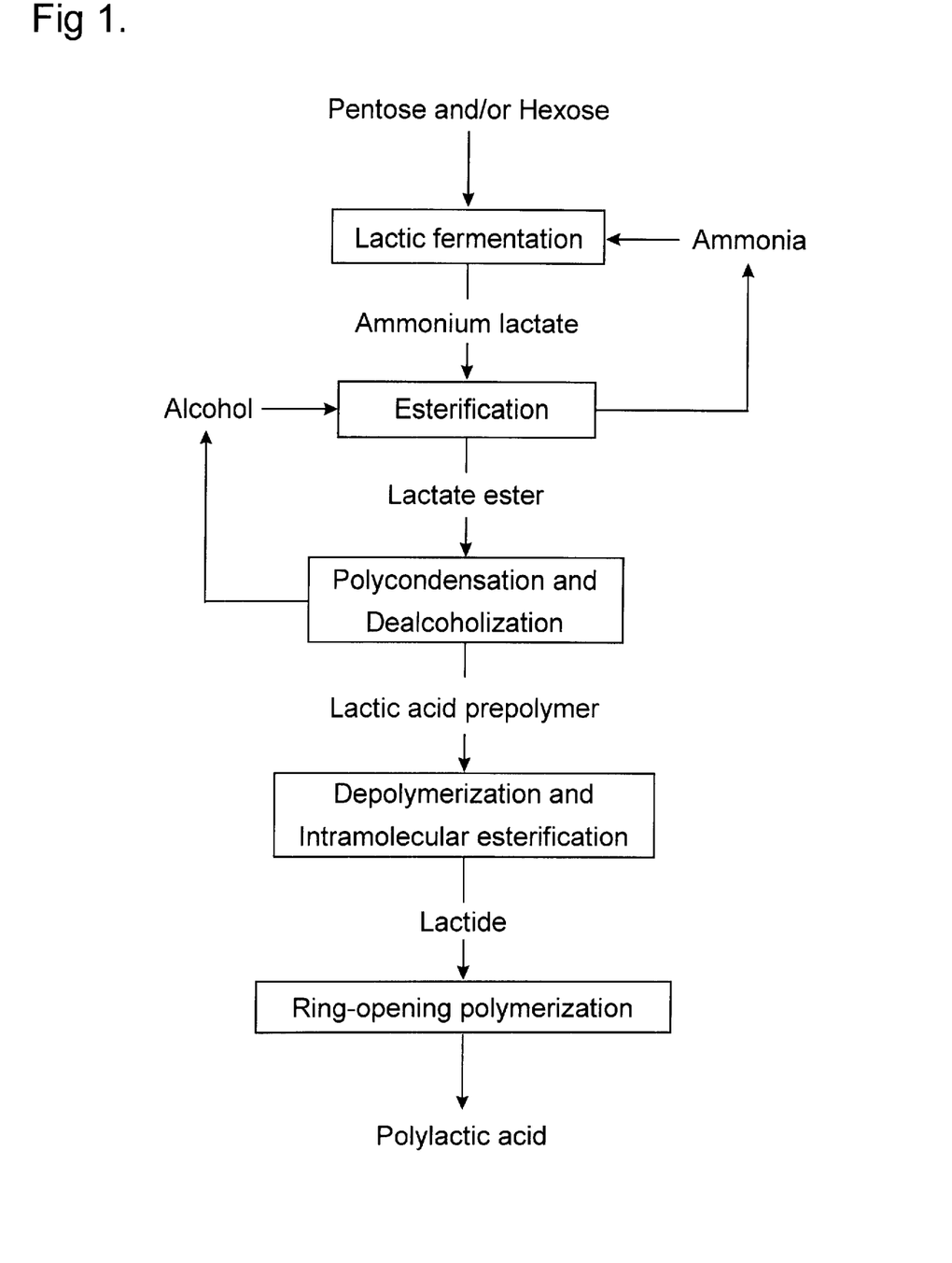
FIG. 1 is a schematic diagram illustrating steps of a process for producing lactide or a process for producing polylactic acid according to the present invention.

In a process for producing lactide or a process for producing polylactic acid according to the present invention, fermented lactic acid is employed. As the lactic acid, there are two optical isomers, L-lactic acid and D-lactic acid, and in the present invention, ammonium salt of any isomer or a mixture thereof may be employed. In accordance with a L/D ratio of ammonium salt employed, a ratio of L-lactide/meso-lactide/D-lactide in the obtained lactide is determined and a ratio of L-lactic acid unit/D-lactic acid unit in the obtained polylactic acid is also determined. Polylactic acid consisting of the L-lactic acid unit or the D-lactic acid unit can be crystallized and melting point of such polylactic acid can be high.

Figure 2:
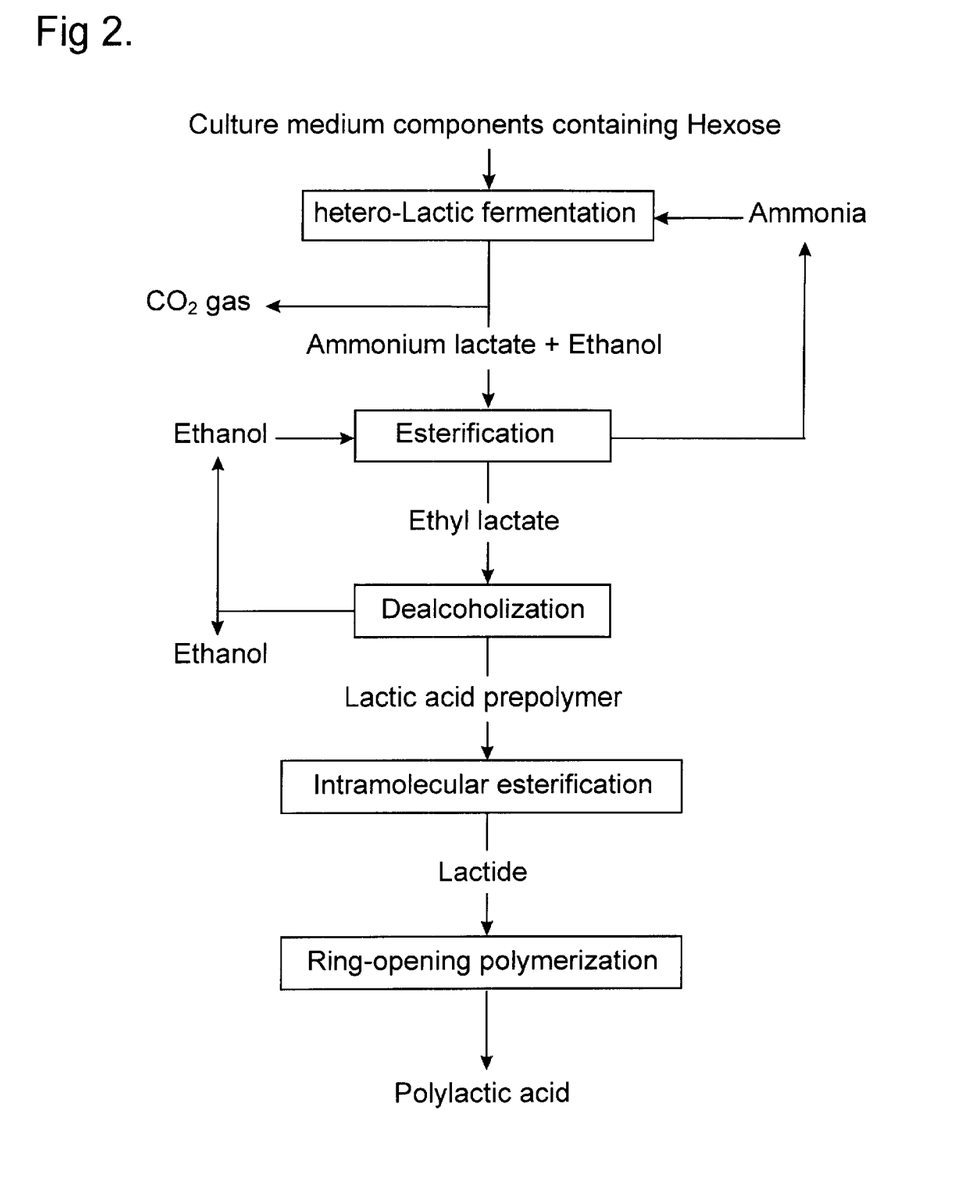
FIG. 2 is a schematic diagram illustrating steps of a process for producing lactide or a process for producing polylactic acid according to the present invention in the case of performing hetero-lactic fermentation of hexose.

Hexose such as glucose may be converted by hetero-lactic fermentation to produce 1 mol of lactic acid and 1 mol of ethanol with generating 1 mol of carbon dioxide gas from 1 mol of glucose. Hetero-lactic fermentation is conducted while neutralizing with ammonia, and the generated ammonium lactate is esterified with alcohol (ethanol) to yield lactate ester (ethyl ester). Ammonia generated at the time of esterification is recovered. Unreacted alcohol (ethanol) is distilled off to perform purification of lactate ester (ethyl ester).

Figure 3:
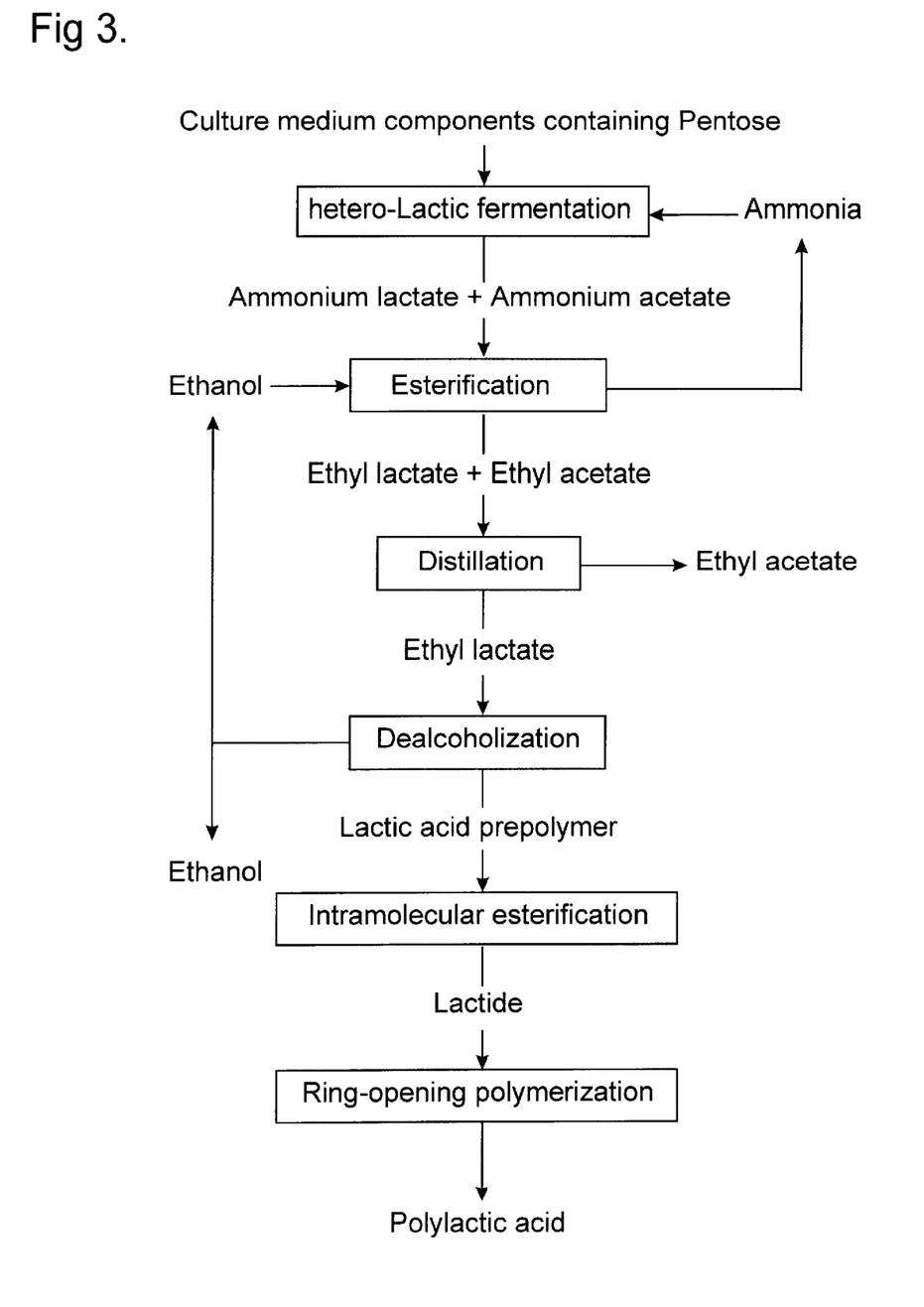
FIG. 3 is a schematic diagram illustrating steps of a process for producing lactide or a process for producing polylactic acid according to the present invention in the case of performing hetero-lactic fermentation of pentose.

Pentose such as xylose may be converted by hetero-lactic fermentation to produce 1 mol of lactic acid and 1 mol of acetic acid from 1 mol of xylose. Hetero-lactic fermentation is conducted while neutralizing with ammonia to yield ammonium lactate and ammonium acetate. Ammonium lactate and ammonium acetate are esterified with ethanol to produce ethyl lactate and ethyl acetate, respectively. Ammonia generated at the time of esterification is recovered. Unreacted ethanol is distilled off, and purification of ethyl lactate is performed by distillation with removing and recovering ethyl acetate. Ethyl acetate is useful as a solvent.

Wood type biomass includes cellulose and hemicellulose, which produces hexose and pentose by saccharification. Thus, saccharified product of wood materials generally contains hexose such as glucose and pentose such as xylose as a mixture. The product may be purified by chromatographic separation, and hetero-lactic fermentation may be conducted employing hexose or pentose as a starting material as described above. Alternatively, a mixture of hexose and pentose may be more preferably employed if possible.

Accordingly, hetero-lactic fermentation of a mixture containing hexose and pentose may be performed. Hetero-lactic fermentation is conducted while neutralizing with ammonia to produce ammonium lactate and ethanol from hexose, and to produce ammonium lactate and ammonium acetate from pentose. Ammonium lactate and ammonium acetate are esterified with ethanol (if amount of ethanol obtained by fermentation is not enough, ethanol might be further added) to yield ethyl lactate and ethyl acetate, respectively. Ammonia generated at the time of esterification is recovered. Unreacted ethanol is distilled off, and purification of ethyl lactate is conducted by distillation with removing and recovering ethyl acetate.

In any case described above, at the time of esterifying ammonium lactate, 1 to 3 mols of alcohol based on 1 mol of ammonium lactate is preferably added. Further, in the case of esterifying with ethanol in particular, a reaction temperature is preferably raised by pressurization. By raising a reaction temperature, a reaction rate can be increased. Furthermore, based on 1 mol of ammonium lactate, 0.1 to 3 mols of water and catalytic amount of strong acid such as sulfuric acid may be added.

As a microorganism capable of conducting homo-type lactic fermentation, some of the Lactobacillus genus, the Streptococcus genus, the Rhizopus genus, the Bacillus genus and others may be mentioned. As a microorganism capable of conducting hetero-type lactic fermentation, the Leuconostoc genus, some of the Lactobacillus genus may be mentioned. In accordance with a strain of the microorganism used, L-lactic acid, D-lactic acid or racemate DL-lactic acid can be obtained, and therefore, the strain may be selected depending on purposes for use.

In the present process, a lactic fermentation liquid neutralized with ammonia water may be used as it is as a starting material, or pretreatment may be conducted by a conventionally known method such as removal of microorganism by centrifugal separation, treatment with active charcoal, extraction with solvent, electrodialysis, membrane filtration, or the like.

(2) Step of Polycondensing Lactate Ester and Dealcoholizing

The obtained lactate ester is polycondensed by heating at 130° C. to 220° C. under a pressure of from an ordinary pressure to reduced pressure with about 5 mmHg to produce a lactic acid oligomer with a weight-average molecular weight of less than 15,000, preferably with a weight-average molecular weight of approximately from 1000 to 3500 (lactic acid prepolymer). The monomer and the lactic acid oligomer generated by the polycondensation are refluxed to remove alcohol (ethanol) to the outside of the reaction system and recover alcohol.

Further, the polycondensing step is preferably conducted by gradually raising a temperature in each stage. For example, a temperature in the first stage of 135±3° C., in the second stage of 150±3° C., and in the third stage of 160±3° C., is preferable (Example 2). The polycondensing step may be performed more stepwise, or may be performed by continuous and gradual increase of a temperature. For example, a temperature is preferably raised in a multi-stage such as in the first stage at 135±3° C., in the second stage at 150±3° C., in the third stage at 160±3° C., in the forth stage at 180±3° C. and in the fifth stage at 200±3° C. (Example 3). Further, a temperature is preferably raised by pressurizing. Furthermore, a polymerization catalyst may be added. Under such condition, a lactic acid oligomer with a weight-average molecular weight of approximately from 1000 to 3500 can be obtained, thereby increasing a difference in a boiling point of between the oligomer and lactide and becoming separation easy.

(3) Step of Depolymerizing Lactic Acid Oligomer and Intramolecular Esterification The obtained lactic acid oligomer is depolymerized and intramolecular esterification (cyclic dimerization) is performed to produce lactide. The depolymerization is conducted in the presence of a depolymerization catalyst other than monobutyltin, by heating the lactic acid oligomer at a temperature of a molten temperature or above of the lactic acid oligomer to be treated, with reducing a pressure to a vapor pressure or below of the lactide at said temperature, so as to distill generated lactide off. Normally, the depolymerization is preferably performed under a reduced pressure of 5 mmHg to 50 mmHg at a temperature of 190° C. to 200° C. By using an apparatus capable of achieving high vacuum level, yield of lactide is improved.

As the polymerization catalyst or the depolymerization catalyst, a catalyst composed of at least one metal or metal compound selected from a group consisting of IA group, IIA group, IIB group, IVA group, IVB group, VA group and VIIA group in the periodic table may be used.

As the catalyst classified into the IA group, for example, a hydroxide of alkali metal (such as, for example, sodium hydroxide, potassium hydroxide, and lithium hydroxide), a salt of alkali metal with weak acid (such as, for example, sodium lactate, sodium acetate, sodium carbonate, sodium octylate, sodium stearate, potassium lactate, potassium acetate, potassium carbonate, and potassium octylate), and an alkoxide of alkali metal (such as, for example, sodium methoxide, potassium methoxide, sodium ethoxide, and potassium ethoxide) may be mentioned.

As the catalyst classified into the IIA group, for example, a calcium salt of organic acid (such as, for example, calcium acetate) may be mentioned.

As the catalyst classified into the IIB group, for example, a zinc salt of organic acid (such as, for example, zinc acetate) may be mentioned.

As the catalyst classified into the IVA group, for example, tin powder may be mentioned as well as an organic tin type catalyst other than monobutyltin (such as, for example, tin lactate, tin tartrate, tin dicaprylate, tin dilaurylate, tin diparmitate, tin distearate, tin dioleate, tin α-naphthoate, tin β-naphthoate, and tin octylate).

As the catalyst classified into the IVB group, for example, a titanium type compound such as tetrapropyl titanate and a zirconium type compound such as zirconium isopropoxide may be mentioned.

As the catalyst classified into the VA group, for example, an antimony type compound such as antimony trioxide may be mentioned.

As the catalyst classified into the VIIA group, for example, a manganese salt of organic acid (such as, for example, manganese acetate) may be mentioned.

All of these described above are conventionally known catalysts for polymelyzation of polylactic acid. Among these, the catalyst composed of tin or tin compound is particularly preferable in a view of catalytic activity.

In the present invention, above-mentioned catalyst is preferably used in an amount of $10^{-4}$ to 1.0 weight % based on the lactic acid oligomer to be treated. More preferable amount is 0.001 to 0.01 weight %.

(4) Step of Ring-Opening Polymerization of Lactide

The ring-opening polymerization of the obtained lactide may be performed by a known method to produce polylactic acid or polylactic acid copolymer. For example, lactide is polymerized in the presence of tin octylate catalyst at 160° C. to 180° C. Polylactic acid with a weight-average molecular weight of about 100,000 to 1,000,000 (GPC, polystyrene conversion) can be obtained.

EXAMPLES

The present invention is further described in the following examples which are not intended to restrict the invention.

Example 1

① Step of Esterifying and Removing Ammonia 472 g of an aqueous ammonium L-lactate solution (68%) produced by a fermentative process and 500 g of ethanol were placed into a 1000 mL flask equipped with a stirrer, a condenser and a thermometer. Ethanol was refluxed for 3 hours while keeping the reaction liquid at a temperature of 90° C. to 100° C., thereby performing esterification. At this time, generated ammonia that was not trapped by the condenser was recovered in a gas-washing bottle that was equipped at the end of the condenser and contained ice-water. Recovery yield of ammonia was 98%.

② Step of Removing Unreacted Ethanol

The reaction liquid obtained in the step ① was kept at a temperature of 80° C. to remove (recover) 360 g of unreacted ethanol by distillation. Next, a temperature of the reaction liquid was raised to 120° C. to distill 150 g of a water content in the reaction liquid off.

③ Step of Purifying Ethyl Lactate

The reaction liquid obtained in the step ② was subjected to simple distillation by reducing a pressure to 50 mmHg and keeping a liquid temperature at 70° C. to 100° C. to obtain 351 g of purified ethyl L-lactate (in 99.2% yield).

④ Step of Polycondensing Ethyl Lactate 236 g of the purified ethyl L-lactate obtained in the step ③ and 1.18 g of tin octylate were placed into a 500 mL flask equipped with a stirrer, a condenser, a thermometer and a tube for introducing a nitrogen gas. A liquid temperature was kept at 160° C. and a pressure was gradually reduced from an ordinary pressure to 200 mmHg under a nitrogen flow by taking 5 hours, thereby distilling off ethanol generated by the polycondensation of ethyl L-lactate. A weight-average molecular weight of the obtained polycondensed product was measured by GPC and found to be 3000.

⑤ Step of Producing Lactide

The reaction liquid obtained in the step ④ was distilled while keeping a pressure of 5 mmHg and a liquid temperature of 200° C. to obtain 142.95 g of LL-lactide as a main fraction (in 99.3% yield with a 99.8% purity).

⑥ Step of Polymerizing 10 g of the lactide obtained in the step ⑤ and 0.25 g of tin octylate were placed into a test tube having a screwed-opening. After the atmosphere was replaced with a nitrogen gas, the test tube was tightly capped and the polymerization was performed at 180° C. for 20 minutes. A weight average molecular weight of the obtained polylactic acid was found to be 250,000 (GPC, polystyrene conversion).

Example 2

① Step of esterifying and removing ammonia, ② step of removing unreacted ethanol and ③ step of purifying ethyl lactate were performed in the same manner as in Example 1.

④ Step of Polycondensing Ethyl Lactate 236 g of the purified ethyl L-lactate obtained in the step ③ was placed into a 500 mL flask equipped with a stirrer, a reflux condenser and a thermometer. A liquid temperature was raised stepwise from 135° C. to 160° C., and a pressure was gradually reduced from an ordinary pressure to 5 mmHg by taking 3 hours. During this period, ethyl L-lactate and an L-lactic acid oligomer generated by the polycondensation of ethyl L-lactate were refluxed in the flask, and a temperature of cooling water in the reflux condenser was raised stepwise from 10° C. to 60° C. so as to remove generated ethanol to the outside of the reaction system. 91 g of ethanol generated at this time was trapped and collected in a cold trap equipped at the end of the reflux condenser. A weight-average molecular weight of the obtained polycondensed product was measured by GPC and found to be 2800.

⑤ Step of Producing Lactide

To a reaction liquid obtained in the step ④ (the L-lactic acid oligomer) was added 1.2 g of tin octylate, and distillation was performed by keeping a pressure of 5 mmHg and a liquid temperature of 200° C. to obtain 142.95 g of LL-lactide as a main fraction (in 99.3% yield with 99.8% purity).

⑥ Step of Polymerizing 10 g of the lactide obtained in the step ⑤ and 0.25 g of tin octylate were placed into a test tube having a screwed-opening. After the atmosphere was replaced with a nitrogen gas, the test tube was tightly capped and the polymerization was performed at 180° C. for 20 minutes. A weight-average molecular weight of the obtained polylactic acid was found to be 250,000 (GPC, polystyrene conversion).

Example 3

① Step of esterifying and removing ammonia, ② step of removing unreacted ethanol, and ③ step of purifying ethyl lactate were performed in the same manner as in Example 1.

④ Step of Polycondensing Ethyl Lactate 236 g of the purified ethyl L-lactate (with an optical purity of 99.7%) obtained in the step ③ was placed into a 500 mL flask equipped with a stirrer, a reflux condenser and a thermometer, and a liquid temperature was raised stepwise from 135° C. to 220° C. under an ordinary pressure. During this period, ethyl L-lactate and an L-lactic acid oligomer generated by the polycondensation of ethyl L-lactate were refluxed in the flask, and a temperature of cooling water in the reflux condenser was set at 85° C. so as to remove generated ethanol to the outside of the reaction system.

Then, a pressure was gradually reduced from an ordinary pressure to 5 mmHg by taking 3 hours. During this period, the L-lactic acid oligomer generated by the polycondensation of ethyl L-lactate was refluxed in the flask, and a temperature of cooling water in the reflux condenser was raised stepwise from 10° C. to 60° C. so as to remove generated ethanol to the outside of the reaction system. 91 g of ethanol generated at this time was trapped and collected in a cold trap equipped at the end of the reflux condenser. A weight-average molecular weight of the obtained polycondensed product was measured by GPC and found to be 2800.

A portion of this polycondensed product was sampled, and hydrolyzed with sodium hydroxide. In lactic acid obtained by the hydrolysis, an optical purity of L-lactic acid was found to be 99.5%. Decrease of the optical purity in the polycondensing step was not observed.

⑤ Step of Producing Lactide

To the reaction liquid obtained in the step ④ the L-lactic acid oligomer) was added 1.2 g of tin octylate, and distillation was performed by keeping a pressure of 5 mmHg and a liquid temperature of 200° C. to obtain 142.95 g of LL-lactide as a main fraction (in 99.3% yield with 99.8% purity).

⑥ Step of Polymerizing 10 g of the lactide obtained in the step ⑤ and 0.25 g of tin octylate were placed into a test tube having a screwed-opening. After the atmosphere was replaced with a nitrogen gas, the test tube was tightly capped and the polymerization was performed at 180° C. for 20 minutes. A weight-average molecular weight of the obtained polylactic acid was found to be 250,000 (GPC, polystyrene conversion).

Example 4

5 L of a culture medium containing 500 g of glucose, 100 g of yeast extracts and 100 g of polypeptone was sterilized by autoclaving, and *Streptococcus feacalis* was implanted thereto. This was cultured at 37° C., and controlled to a pH 7.0 by 6N ammonia water. The cultures were finished after approximately 15 hours, and the culture fluid was concentrated. To the concentrated culture fluid was added 1000 g of ethanol, and ethanol was refluxed for 3 hours by keeping a temperature of 90° C. to 100° C. At this time, generated ammonia that was not trapped by the condenser was recovered by a gas-washing bottle that was equipped at the end of the condenser and contained ice-water. Recovery yield of ammonia was 98%. The obtained reaction liquid was kept at a temperature of 80° C. to remove (recover) 750 g of unreacted ethanol by distillation. Subsequently, a temperature of the reaction liquid was raised to 120° C. to distill 120 g of a water content in the reaction liquid off.

The obtained reaction liquid was subjected to simple distillation by reducing a pressure to 50 mmHg and keeping a liquid temperature at 70° C. to 100° C. to obtain 650 g of purified ethyl L-lactate.

650 g of the purified ethyl L-lactate obtained and 3.3 g of tin octylate were placed into a 1000 mL flask equipped with a stirrer, a condenser, a thermometer and a tube for introducing a nitrogen gas. A liquid temperature was kept at 160° C., and a pressure was gradually reduced from an ordinary pressure to 200 mmHg under a nitrogen flow by taking 5 hours, thereby distilling off 250 g of ethanol generated by the polycondensation of ethyl L-lactate. A weight-average molecular weight of the obtained polycondensed product was measured by GPC and found to be 3200.

The obtained reaction liquid was distilled while keeping a pressure of 5 mmHg and a temperature of 200° C. to obtain 393 g of LL-lactide as a main fraction.

10 g of the obtained LL-lactide and 0.25 g of tin octylate were placed into a test tube having a screwed-opening. After the atmosphere was replaced with a nitrogen gas, the test tube was tightly capped and the polymerization was performed at 180° C. for 20 minutes. A weight-average molecular weight of the obtained polylactic acid was found to be 200,000 (GPC, polystyrene conversion).

Example 5

4 L of a culture medium containing 400 g of xylose derived from a wood material, 80 g of yeast extracts and 80 g of polypeptone was sterilized by autoclaving, and the Leuconostoc genus was implanted thereto. This was cultured at 37° C., and controlled to a pH 7.0 by 6N ammonia water. The cultures were finished after approximately 25 hours, and the culture fluid was concentrated. To the concentrated culture fluid was added 500 g of ethanol, and ethanol was refluxed for 3 hours by keeping a temperature of 90° C. to 100° C. At this time, generated ammonia that was not trapped by the condenser was recovered by a gas-washing bottle that was equipped at the end of the condenser and contained ice-water. Recovery yield of ammonia was 98%. The obtained reaction liquid was kept at a temperature of 80° C. to distill 250 g of unreacted ethanol off. Subsequently, a temperature of the reaction liquid was raised to 120° C. to distill 75 g of a water content in the reaction liquid off.

The obtained reaction liquid was subjected to simple distillation by reducing a pressure to 50 mmHg and keeping a liquid temperature at 70° C. to 100° C. to obtain 310 g of purified ethyl L-lactate and 230 g of ethyl acetate.

310 g of the purified ethyl L-lactate obtained and 1.5 g of tin octylate were placed into a 1000 mL flask equipped with a stirrer, a condenser, a thermometer and a tube for introducing a nitrogen gas. A liquid temperature was kept at 160° C., and a pressure was gradually reduced from an ordinary pressure to 200 mmHg under a nitrogen flow by taking 5 hours, thereby distilling off 120 g of ethanol generated by the polycondensation of ethyl L-lactate. (120 g of fresh ethanol was obtained.) A weight-average molecular weight of the obtained polycondensed product was measured by GPC and found to be 2900.

The obtained reaction liquid was distilled while keeping a pressure of 4 mmHg and a liquid temperature of 210° C. to obtain 283 g of LL-lactide as a main fraction.

10 g of the obtained L-lactide and 0.25 g of tin octylate were placed into a test tube having a screwed-opening. After the atmosphere was replaced with a nitrogen gas, the test tube was tightly capped and the polymerization was performed at 180° C. for 20 minutes. A weight-average molecular weight of the obtained polylactic acid was found to be 190,000 (GPC, polystyrene conversion).

Example 6

4 L of a culture medium containing 50 g of xylose derived from a wood material, 350 g of glucose, 80 g of yeast extracts and 80 g of polypeptone was sterilized by autoclaving, and the Leuconostoc genus was implanted thereto. This was cultured at 37° C., and controlled to a pH 7.0 by 6N ammonia water. The cultures were finished after approximately 30 hours, and the culture fluid was concentrated. To the concentrated culture fluid was added 400 g of ethanol, and ethanol was refluxed for 3 hours by keeping a temperature of 90° C. to 100° C. At this time, generated ammonia that was not trapped by the condenser was recovered by a gas-washing bottle that was equipped at the end of the condenser and contained ice-water. Recovery yield of ammonia was 97%. The obtained reaction liquid was kept at a temperature of 80° C. to distill 426 g of unreacted ethanol off. Subsequently, a temperature of the reaction liquid was raised to 120° C. to distill 60 g of a water content in the reaction liquid off.

The obtained reaction liquid was subjected to simple distillation by reducing a pressure to 50 mmHg and keeping a liquid temperature at 70° C. to 100° C. to obtain 260 g of purified ethyl L-lactate, 20 g of ethyl acetate and 426 g of ethanol.

260 g of the purified ethyl L-lactate obtained and 1.3 g of tin octylate were placed into a 1000 mL flask equipped with a stirrer, a condenser, a thermometer and a tube for introducing a nitrogen gas. A liquid temperature was kept at 160° C., and a pressure was gradually reduced from an ordinary pressure to 200 mmHg under a nitrogen flow by taking 5 hours, thereby distilling off 100 g ethanol generated by the polycondensation of ethyl L-lactate. A weight-average molecular weight of the obtained polycondensed product was measured by GPC and found to be 2500.

The obtained reaction liquid was distilled while keeping a pressure of 5 mmHg and a liquid temperature of 200° C. to obtain 314 g of LL-lactide as a main fraction.

10 g of the obtained LL-lactide and 0.25 g of tin octylate were placed into a test tube having a screwed-opening. After the atmosphere was replaced with a nitrogen gas, the test tube was tightly capped and the polymerization was performed at 180° C. for 20 minutes. A weight-average molecular weight of the obtained polylactic acid was found to be 220,000 (GPC, polystyrene conversion).

The present invention can be embodied in many other ways without departing from the spirit and the major aspects of the invention. Accordingly, the examples described above are only illustrative and should not be interpreted to be limitative. Furthermore, any modification within the scope of the appended claims is encompassed in the invention.

What is claimed is:

1. A process for producing lactide, which comprises the steps of: (1) synthesizing lactate ester from ammonium lactate obtained by lactic fermentation; (2) polycondensing the lactate ester in the presence of a catalyst other than monobutyltin, whereby polylactic acid with a weight-average molecular weight of less than 15,000 (lactic acid prepolymer) is synthesized; and (3) depolymerizing the polylactic acid, whereby lactide is produced.

2. The process for producing lactide according to claim 1, wherein the step (1) comprises: allowing the ammonium lactate obtained by lactic fermentation to react with alcohol, whereby lactate ester is synthesized; and recovering ammonia.

3. The process for producing lactide according to claim 1, wherein the step (1) comprises: allowing the ammonium lactate obtained by lactic fermentation to react with alcohol other than alcohol of which the number of carbon atoms is 4 or 5, whereby lactate ester is synthesized; and recovering ammonia.

4. The process for producing lactide according to claim 1, wherein the step (1) comprises: allowing the ammonium lactate obtained by lactic fermentation to react with ethanol under a pressurized condition, whereby ethyl lactate is synthesized; and recovering ammonia.

5. The process for producing lactide according to claim 1, wherein the step (1) comprises: allowing an aqueous solution of the ammonium lactate obtained by lactic fermentation to react with alcohol of which the number of carbon atoms is 4 or more in a reactor under reflux, in which the alcohol is separable from water to form two layers with water;

trapping at least a portion of condensed water and at least a portion of condensed alcohol in a separator; discharging at least a portion of the water trapped in the separator as a lower layer; adding fresh water to the separator and returning at least a portion of the alcohol trapped in the separator as an upper layer into the reactor; and repeating this series of the procedures, whereby lactate ester is synthesized; and recovering ammonia.

6. The process for producing lactide according to claim 1, wherein the step (1) comprises: allowing an aqueous solution of the ammonium lactate obtained by lactic fermentation to react with alcohol of which the number of carbon atoms is 4 or more in a reactor under reflux, in which the alcohol is separable from water to form two layers with water; distilling off a portion of the alcohol or the whole alcohol continuously; and adding fresh alcohol to the reactor, whereby lactate ester is synthesized; and recovering ammonia.

7. The process for producing lactide according to claim 1, wherein the step (1) comprises: allowing the ammonium lactate obtained by lactic fermentation to react with ethanol; after completing the reaction, distilling off ethanol and ethyl lactate, respectively;

adding fresh ethanol to a remained solution of the ammonium lactate or adding fresh ethanol and fresh ammonium lactate obtained by lactic fermentation to the remained solution of the ammonium lactate; allowing the ammonium lactate to react with ethanol again; and repeating this reaction procedure, whereby ethyl lactate is synthesized; and recovering ammonia.

8. The process for producing lactide according to claim 1, wherein the polycondensation in the step (2) is conducted while refluxing the lactate ester and/or the polylactic acid (lactic acid prepolymer) which is a polycondensed product of the lactate ester.

9. The process for producing lactide according to claim 1, wherein the step (2) comprises: polycondensing the lactate ester, whereby the lactic acid prepolymer is obtained; and recovering generated alcohol.

10. The process for producing lactide according to claim 1, wherein the step (2) comprises raising a temperature of a reactor continuously in the step of polycondensing the lactate ester.

11. The process for producing lactide according to claim 1, wherein the step (1) comprises: culturing a microorganism capable of conducting hetero-lactic fermentation in a culture medium containing hexose while controlling a pH value with ammonia to produce the ammonium lactate and ethanol; and allowing the ammonium lactate to react with alcohol, whereby lactate ester is synthesized; and recovering ammonia.

12. The process for producing lactide according to claim 1, wherein the step (1) comprises: culturing a microorganism capable of conducting hetero-lactic fermentation in a culture medium containing hexose while controlling a pH value with ammonia to produce the ammonium lactate and ethanol; and allowing the ammonium lactate to react with alcohol other than alcohol of which the number of carbon atoms is 4 or 5, whereby lactate ester is synthesized; and recovering ammonia.

13. The process for producing lactide according to claim 1, wherein the step (1) comprises: culturing a microorganism capable of conducting hetero-lactic fermentation in a culture medium containing pentose while controlling a pH value with ammonia to produce ammonium lactate and ammonium acetate;

allowing the ammonium lactate and the ammonium acetate to react with ethanol, whereby ethyl lactate and ethyl acetate are synthesized, respectively; recovering ammonia; and further removing ethyl acetate by distillation; and wherein the step (2) comprises: polycondensing the ethyl lactate, whereby the lactic acid prepolymer is obtained; and recovering ethanol.

14. The process for producing lactide according to claim 1, wherein the step (1) comprises: culturing a microorganism capable of conducting hetero-lactic fermentation in a culture medium containing pentose and hexose while controlling a pH value with ammonia to produce ammonium lactate, ethanol and ammonium acetate;

allowing the ammonium lactate and the ammonium acetate to react with ethanol, whereby ethyl lactate and ethyl acetate are synthesized, respectively; recovering ammonia; and further removing the ethyl acetate by distillation; and wherein the step (2) comprises: polycondensing the ethyl lactate, whereby the lactic acid prepolymer is obtained; and recovering ethanol.

15. A process for producing polylactic acid, which comprises ring-opening polycondensing lactide obtained by a process according to claim 1, whereby polylactic acid is obtained.

16. A process for producing lactic acid prepolymer, which comprises the steps of: (1) synthesizing lactate ester from ammonium lactate obtained by lactic fermentation; and (2) polycondensing the lactate ester in the presence of a catalyst other than monobutyltin, in which said polycondensation is conducted while refluxing the lactate ester and/or polylactic acid (lactic acid prepolymer) which is a polycondensed product of the lactate ester, whereby polylactic acid with a weight-average molecular weight of less than 15,000 (lactic acid prepolymer) is synthesized.

* * * * *